US012106186B2

(12) United States Patent
Neumann

(10) Patent No.: US 12,106,186 B2
(45) Date of Patent: Oct. 1, 2024

(54) METHOD OF AND SYSTEM FOR AN INTERACTIVE SYSTEM FOR ACTIVITY QUANTIFICATION

(71) Applicant: KPN INNOVATIONS, LLC., Lakewood, CO (US)

(72) Inventor: Kenneth Neumann, Lakewood, CO (US)

(73) Assignee: KPN Innovations, LLC, Lakewood, CO (US)

(*) Notice: Subject to any disclaimer, the term of this patent is extended or adjusted under 35 U.S.C. 154(b) by 1126 days.

(21) Appl. No.: 16/919,633

(22) Filed: Jul. 2, 2020

(65) Prior Publication Data
US 2022/0004915 A1 Jan. 6, 2022

(51) Int. Cl.
G06N 20/00 (2019.01)
A61B 5/11 (2006.01)
(Continued)

(52) U.S. Cl.
CPC ............. *G06N 20/00* (2019.01); *G16H 20/00* (2018.01); *G16H 50/70* (2018.01); *A61B 5/1118* (2013.01)

(58) Field of Classification Search
CPC ......... G06N 20/00; G16H 50/70; G16H 20/00
See application file for complete search history.

(56) References Cited

U.S. PATENT DOCUMENTS 9,504,408 B2  11/2016  Hong et al.
9,693,724 B2   7/2017  Dagum
(Continued)

FOREIGN PATENT DOCUMENTS

WO  WO2019040908  2/2019

OTHER PUBLICATIONS

Casaccia, Sara, et al. "Measurement of users' well-being through domotic sensors and machine learning algorithms." IEEE Sensors Journal 20.14 (2020): 8029-8038. (Year: 2020).*

(Continued)

*Primary Examiner* — Kevin W Figueroa
(74) *Attorney, Agent, or Firm* — Caldwell Intellectual Property Law

(57) ABSTRACT

An interactive system for activity quantification, the system comprising a computing device, wherein the computing device is configured to receive user constitutional data. Computing device may generate a plurality of constitutional component quantifiers by receiving component training data, train a component machine-learning model as a function of the training data, and generate the constitutional component quantifier. Computing device may calculate a comprehensive quantifier as a function of the plurality of constitutional component quantifiers, receive comprehensive training data, train a comprehensive machine-learning model as a function of the training data, and calculate the comprehensive quantifier. Computing device may display, at a user device, the comprehensive quantifier and the constitutional component quantifiers, receive a user selection of at least a constitutional component quantifier, and collect user activity data. Computing device may regenerate a constitutional component quantifier and recalculate the comprehensive quantifier as a function of the recalculated constitutional component quantifier.

20 Claims, 8 Drawing Sheets

(51) Int. Cl.
*G16H 20/00* (2018.01)
*G16H 50/70* (2018.01)

(56) References Cited

U.S. PATENT DOCUMENTS

| | | |
|---|---|---|
| 9,824,190 B2 | 11/2017 | Sudharsan |
| 9,852,266 B2 | 12/2017 | Damani et al. |
| 9,892,576 B2 | 2/2018 | Kursun et al. |
| 10,231,622 B2 | 3/2019 | Soyao et al. |
| 10,265,028 B2 | 4/2019 | Moturu et al. |
| 2007/0055551 A1 | 3/2007 | Szabo |
| 2008/0120267 A1 | 5/2008 | Chen et al. |
| 2008/0306770 A1 | 12/2008 | Sysko et al. |
| 2014/0099614 A1 | 4/2014 | Hu et al. |
| 2014/0257055 A1 | 9/2014 | Pacione et al. |
| 2015/0057634 A1 | 2/2015 | Mastrototaro et al. |
| 2016/0321413 A1 | 11/2016 | Cheyne |
| 2017/0147788 A1 | 5/2017 | Ohnemus et al. |
| 2017/0249445 A1 | 8/2017 | Devries et al. |
| 2019/0336824 A1* | 11/2019 | Fung .................. A63B 22/0285 |

OTHER PUBLICATIONS https://ieeexplore.ieee.org/abstract/document/8321934.
https://www.himss.org/resources/wearable-technology-applications-healthcare-literature-review.

* cited by examiner

METHOD OF AND SYSTEM FOR AN INTERACTIVE SYSTEM FOR ACTIVITY QUANTIFICATION

FIELD OF THE INVENTION

The present invention generally relates to the field of machine-learning. In particular, the present invention is directed to an interactive system for activity quantification.

BACKGROUND

Machine-learning methods are increasingly valuable for analysis of patterns and problem-solving using large quantities of data. However, where the data is large and varied enough, optimizing instruction sets, programs, and the like, for users from machine-learning outputs can become untenable, especially with tradeoffs between sophistication and efficiency.

SUMMARY OF THE DISCLOSURE

In an aspect, an interactive system for activity quantification, the system comprising a computing device, wherein the computing device is configured to receive a plurality of user constitutional data. Computing device may generate a plurality of constitutional component quantifiers, wherein generating each constitutional component quantifier further comprises receiving component training data, the component training data including a plurality of entries correlating constitutional data with component quantifier data, training a component machine-learning model as a function of the component training data, and generating the constitutional component quantifier as a function of the user constitutional data and the component machine-learning model. Computing device may calculate a comprehensive quantifier as a function of the plurality of constitutional component quantifiers, wherein calculating further comprises receiving comprehensive training data, the comprehensive training data including a plurality of entries correlating component quantifier data with comprehensive score data, training a comprehensive machine-learning model as a function of the comprehensive training data, and calculating the comprehensive quantifier as a function of the plurality of constitutional component quantifiers and the comprehensive machine-learning model. Computing device may display, at a user device, the comprehensive quantifier and the plurality of constitutional component quantifiers. Computing device may receive a user selection of at least a constitutional component quantifier, collect user activity data, regenerate the at least a constitutional component quantifier as a function of the user activity data, and recalculate the comprehensive quantifier as a function of the recalculated at least a constitutional component quantifier.

In another aspect, a method for activity quantification, the system comprising a computing device, wherein the computing device is configured to receive a plurality of user constitutional data. Computing device may generate a plurality of constitutional component quantifiers, wherein generating each constitutional component quantifier further comprises receiving component training data, the component training data including a plurality of entries correlating constitutional data with component quantifier data, training a component machine-learning model as a function of the component training data, and generating the constitutional component quantifier as a function of the user constitutional data and the component machine-learning model. Computing device may calculate a comprehensive quantifier as a function of the plurality of constitutional component quantifiers, wherein calculating further comprises receiving comprehensive training data, the comprehensive training data including a plurality of entries correlating component quantifier data with comprehensive score data, training a comprehensive machine-learning model as a function of the comprehensive training data, and calculating the comprehensive quantifier as a function of the plurality of constitutional component quantifiers and the comprehensive machine-learning model. Computing device may display, at a user device, the comprehensive quantifier and the plurality of constitutional component quantifiers. Computing device may receive a user selection of at least a constitutional component quantifier, collect user activity data, regenerate the at least a constitutional component quantifier as a function of the user activity data, and recalculate the comprehensive quantifier as a function of the recalculated at least a constitutional component quantifier.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for an interactive system for activity quantification. In an embodiment, system may generate a series of values relating user data to activity quantifiers using machine-learning models. Machine-learning models may be trained with data relating how user data may be quantified as it relates to the effect activities may have on a quantifier. A machine-learning model may be trained in determining activities that could improve and/or decrease a quantifier and generate a program of activities for a user to follow, and/or provide a plurality of options and prompt a user to select program activities. User adherence to a program may be determined by a machine-learning process, such as a machine-learning model that may determine a program's effectiveness in improving a quantifier, and such a model could alter a user score based on user activity in adhering to a program.

Figure 1:
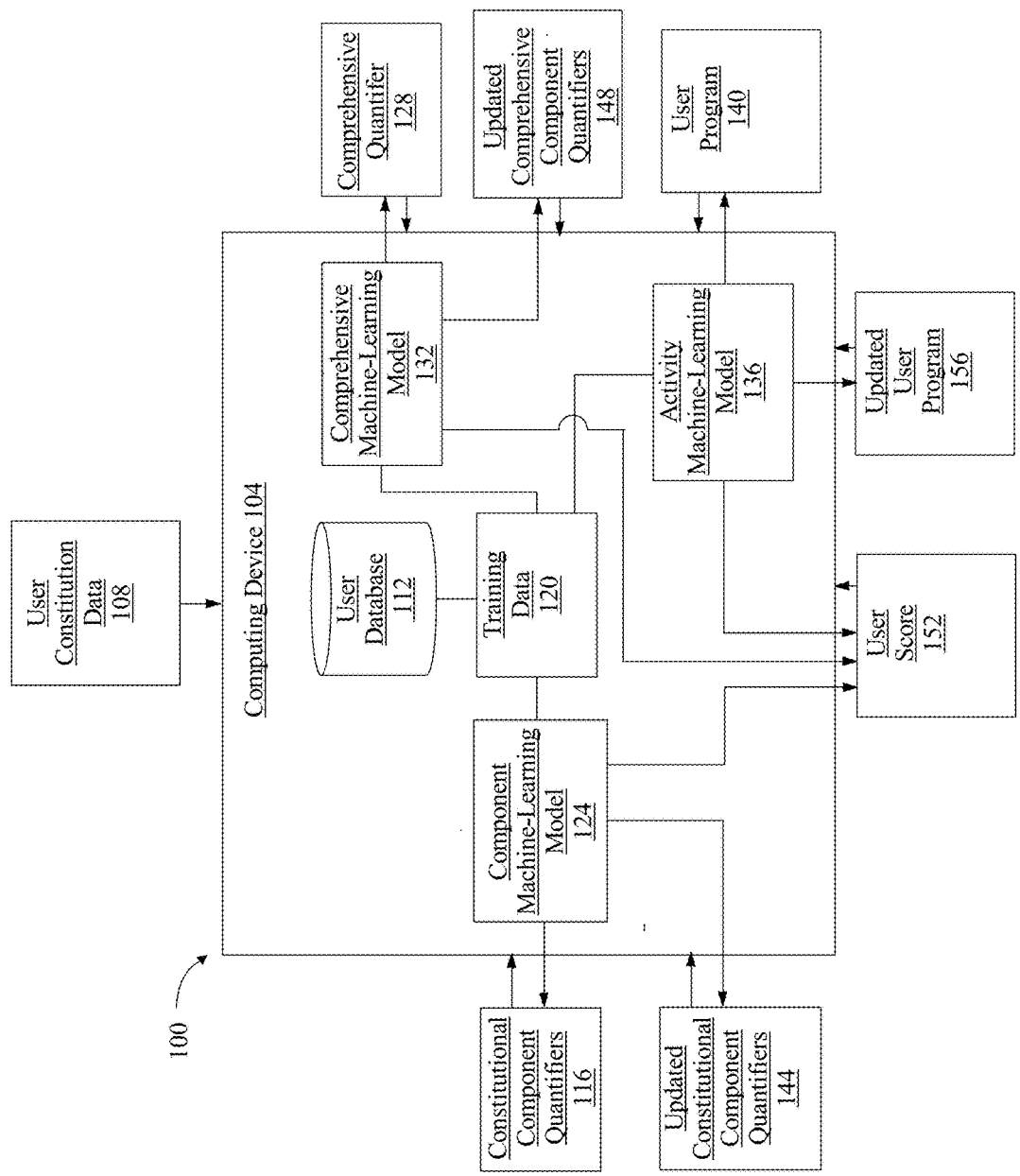
FIG. 1 is a block diagram illustrating an exemplary embodiment of an interactive system for activity quantification.

Referring now to FIG. 1, an exemplary embodiment of a system 100 for an interactive system for activity quantification is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 is configured to receive a plurality of user constitutional data 108. User constitutional data 108 may include at least an element of user-reported data from a questionnaire and/or at least an element of data retrieved from a wearable device. As used in this disclosure "user constitutional data" may refer to any physiological and/or biological parameter relating to a user including, for instance and without limitation, physical and demographic parameters such as age, sex, height, weight, fitness level; biochemical parameters such as blood chemistry and nutritional deficiencies; health parameters including body mass index, blood pressure, pulse, sleep quality, and any other physiological and/or biological parameter. An element of user constructional data 108 may originate from user-reported data. In non-limiting illustrative examples, user-reported data may be received from a questionnaire, for instance as a field-entry form that prompts users to input or report parameters. Alternatively or additionally, an element of user constitutional data 108 may originate from data from a wearable device. As used in this disclosure "data from a wearable device" may refer to any device or device that monitors, collects, records, stores, displays, or otherwise communicates physiological and/or biological data pertaining to a user, for instance and without limitation, an accelerometer, pedometer, gyrometer, electrocardiography (ECG) monitor, pacemaker, electroencephalography (EEG) monitor, bioimpedance monitor, and/or any other device suitable as a wearable physiological and/or biological monitoring device. Computing device 104 may receive user constitutional data 108 via a user database 112, as described in further detail below.

Figure 2:
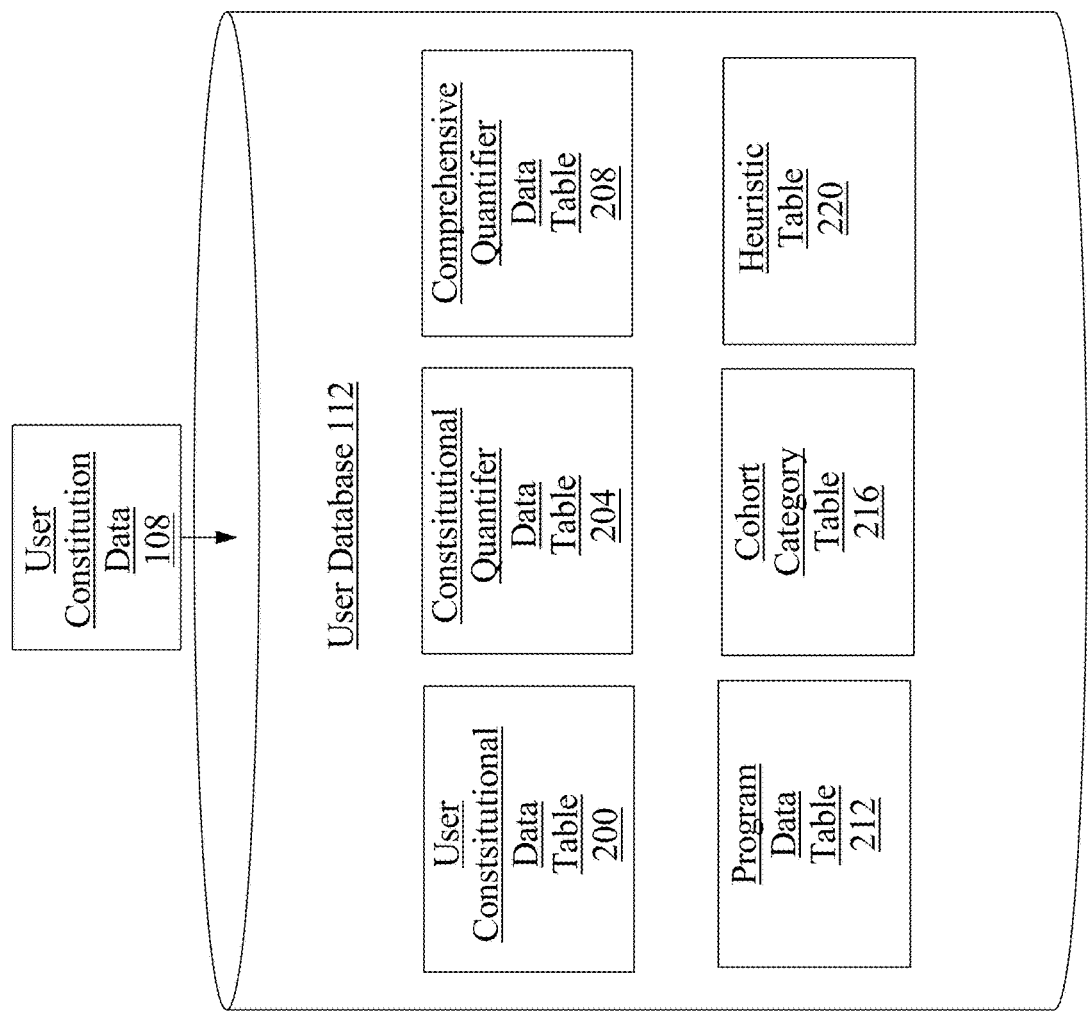
FIG. 2 is a block diagram illustrating an exemplary embodiment of a user database.

Referring now to FIG. 2, a non-limiting exemplary embodiment of a user database 112 is illustrated. User database 112 may be implemented, without limitation, as a relational database, a key-value retrieval database such as a NOSQL database, or any other format or structure for use as a database that a person skilled in the art would recognize as suitable upon review of the entirety of this disclosure. User database 112 may alternatively or additionally be implemented using a distributed data storage protocol and/or data structure, such as a distributed hash table or the like. User database 112 may include a plurality of data entries and/or records as described above. Data entries in a user database 112 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Further referring to FIG. 2, user database 112 may include, without limitation, a user constitutional data table 200, constitutional quantifier data table 204, comprehensive quantifier data table 208, program data table 212, cohort category table 216, and/or heuristic table 220. Determinations by a machine-learning process, machine-learning model, and/or objective function may also be stored and/or retrieved from the user database 112, for instance in non-limiting examples a classifier describing a subset of user constitutional data 108 as it relates to program activities, as described in further detail below. Determinations by a machine-learning model for calculating a constitutional quantifier and/or a comprehensive qualifier may also be stored and/or retrieved from the user database 112, as described in further detail below. As a non-limiting example, user database 112 may organize data according to one or more instruction tables. One or more user database 112 tables may be linked to one another by, for instance in a non-limiting example, common column values. For instance, a common column between two tables of user database 112 may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Still referring to FIG. 2, in a non-limiting embodiment, one or more tables of a user database 112 may include, as a non-limiting example, a user constitutional data table 200, which may include wearable device data, user-reported physiological data, and the like, for use in determining constitutional quantifiers, user program activities, and the like, correlating user data to other tables, entries indicating degrees of relevance to and/or efficacy in calculating a quantifier and/or activity, steps of a program, and/or other elements of data computing device 104 and/or system 100 may use to determine usefulness and/or relevance of user data in determining quantifiers, user activity, scores, and/or activities in user programs as described in this disclosure. One or more tables may include a constitutional component quantifier data table 204, which may include a history of numerical values, metrics, functions, vectors, matrices, and the like, for instance and without limitation, that quantify or otherwise summarize user physiology, for instance a history and tabulation of sleep quality scores determined from a combination of EEG, ECG, bioimpedance, and user-reported data. One or more tables may include a comprehensive quantifier data table 208, which may correlate user data, activities, outcomes, models, heuristics, scores and/or combinations thereof as they may correspond to an overall numerical values, metrics, functions, vectors, matrices, and the like, that corresponds to an overall measure of user physiology and wellness that can be used to determine user program effectiveness, feasibility, and the like. One or more tables may include, without limitation, a program table 212 which may contain one or more inputs identifying one or more categories of data, for instance numerical values and/or steps describing the number and type of user activities for increasing and/or decreasing comprehensive quantifiers, constitutional and/or component quantifiers. One or more tables may include, without limitation, a cohort category table 216 which may contain one or more inputs identifying one or more categories of data, for instance subsets of user constitutional data from one or more users with regard to optimization and generation of objective functions, machine-learning models, scoring functions, ranking functions, and/or user programs as a result of, for instance and without limitation, outputting elements and/or other user data input elements. One or more tables may include, without limitation, a heuristic table 220, which may include one or more inputs describing potential mathematical relationships between at least an element of user data and objectives, instructions, and rankings thereof, change in quantifiers and/or user program over time, and/or objective functions for determining comprehensive quantifier improvement and/or penalization, as described in further detail below.

Referring now to FIG. 1, computing device 104 may generate the constitutional component quantifier 116 as a function of the user constitutional data 108 and the component machine-learning model 124. A "constitutional component quantifier," as described in this disclosure refers to a numerical value, metric, function, vector, matrix, and the like, that describes constitutional data as it relates to a constitutional component of a user, which may be for instance and without limitation, physical fitness, macronutrient goals, sleep quality, mental endurance, and the like. In non-limiting illustrative examples, a constitutional component qualifier 116 may be a quantification of user physical fitness, ability, athleticism, and/or aptitude, determined by a combination of wearable device data corresponding to pulse rate, respiration, blood pressure, pedometer, accelerometer, and gyrometer data recorded during strenuous exercise. In such an example, a component machine-learning model may be trained as a function of such training data 120 to quantify relationships and/or metrics that exist between the data and a score of user physical conditioning and athleticism. In non-limiting examples, a component machine-learning model 124 trained in such a manner may generate an output of a mathematical function that relates certain user activities to various levels of return-on-investment increases in physical conditioning scores as evidenced by the wearable data and user input. Trained component machine-learning models 124 and their associated function, outputs, and the like may be stored and/or retrieved from a user database 120 by a computing device 104 for subsequent use, as described above.

Figure 3:
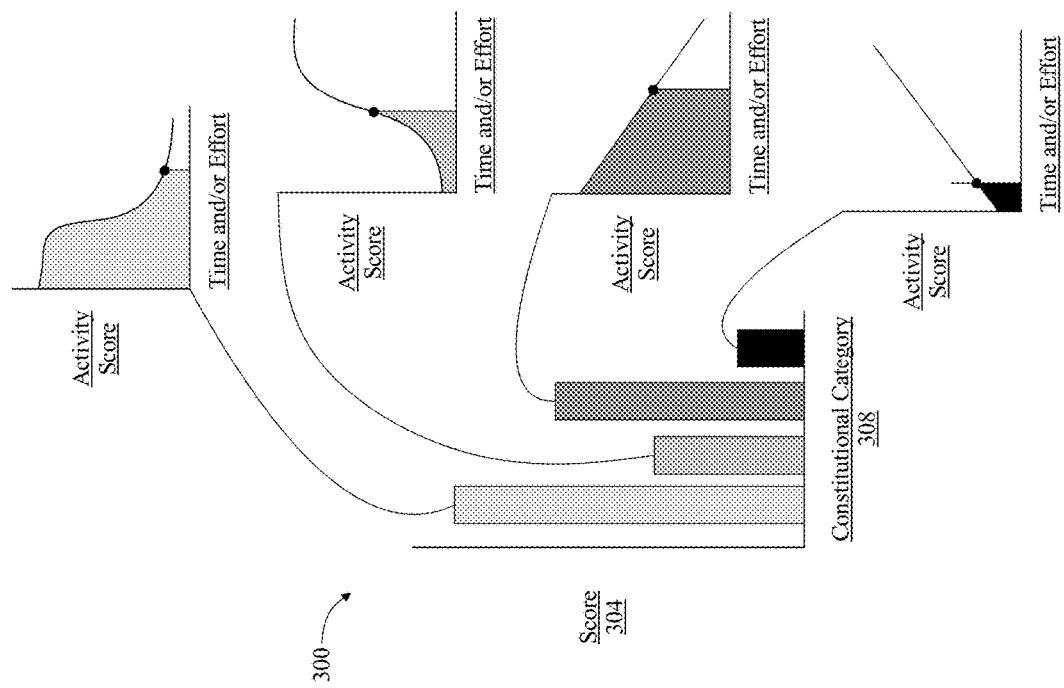
FIG. 3 is a diagrammatic representation of an exemplary embodiment of a plurality of constitutional component quantifiers.

Referring now to FIG. 3, an exemplary embodiment of a plurality of constitutional component quantifiers 300 is illustrated. In non-limiting illustrative examples, each bar of the bar graph may represent a score 304 such as a user score, quantifier, or the like. A score 304 may be, for instance and without limitation, represented as a numerical value on a decimal scale, as it corresponds to a particular constitutional category 308, such as a series of fitness activities. In such an example, each constitutional category 308 score 304 corresponds to a quantifier generated by a component machine-learning model 124, for instance and without limitation as depicted graphically by the four functions; each function represents user constitutional data (such as raw data from a wearable device) that relates time and/or effort spent performing an activity to an activity score, wherein the constitutional quantifier that is assigned to a particular activity is the summation of time and/or activity dedicated to that activity, as illustrated by area-under-the-curve. In non-limiting illustrative examples, a component machine-learning model 124 may contain any number of function, such as the ones depicted, measuring, calculating, or otherwise quantifying relationships between user activity and some numerical score relating the level of performing said activity. For example in FIG. 3, the second function from the top may relate to weight training activity for a user, wherein there is an exponential increase in the utility to the user, and thus in score, at the user's current fitness level; however, following a weight training program will eventually lead to diminished gains as evidenced by the plateau, wherein a constitutional machine-learning model 124 would be able to determine when the plateau begins according to user constitutional data associated with weight training activity. This information may be reflected in determining activities for a user program, as described in further detail below.

Referring again to FIG. 1, generating each constitutional component quantifier 116 may include receiving component training data 120, wherein training data 120 may include a plurality of entries correlating constitutional data with component quantifier data, and training a component machine-learning model 124 as a function of the component training data 120. A machine-learning model, such as a component machine-learning model 124 for generating a constitutional component quantifier 116, may be generated using a machine learning module, as described in further detail below.

Continuing in reference to FIG. 1, "training data," as used herein, is data containing correlations that a machine-learning process may use to model relationships between two or more categories of data elements. For instance, and without limitation, training data 120 may include a plurality of data entries, each entry representing a set of data elements that were recorded, received, and/or generated together; data elements may be correlated by shared existence in a given data entry, by proximity in a given data entry, or the like. Multiple data entries in training data 120 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 120 according to various correlations; correlations may indicate causative and/or predictive links between categories of data elements, which may be modeled as relationships such as mathematical relationships by machine learning processes as described in further detail below. Training data 120 may be formatted and/or organized by categories of data elements, for instance by associating data elements with one or more descriptors corresponding to categories of data elements. As a non-limiting example, training data 120 may include data entered in standardized forms by persons or processes, such that entry of a given data element in a given field in a form may be mapped to one or more descriptors of categories. Elements in training data 120 may be linked to descriptors of categories by tags, tokens, or other data elements; for instance, and without limitation, training data 120 may be provided in fixed-length formats, formats linking positions of data to categories such as comma-separated value (CSV) formats and/or self-describing formats such as extensible markup language (XML), enabling processes or devices to detect categories of data.

Alternatively or additionally, training data 120 may include one or more elements that are not categorized; that is, training data 120 may not be formatted or contain descriptors for some elements of data. Machine learning algorithms and/or other processes may sort training data 120 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 120 to be made applicable for two or more distinct machine learning algorithms as described in further detail below. Training data 120 used by computing device 104 may correlate any input data as described in this disclosure to any output data as described in this disclosure. Training data may contain entries, each of which correlates a machine learning process input to a machine learning process output, for instance without limitation, one or more elements of meal ingredients to a task chain. Training data may be obtained from previous iterations of machine-learning processes, user database 112, user inputs, and/or expert inputs. Training a machine-learning model using training data may be performed using a machine learning module, as described in further detail below.

Figure 4:
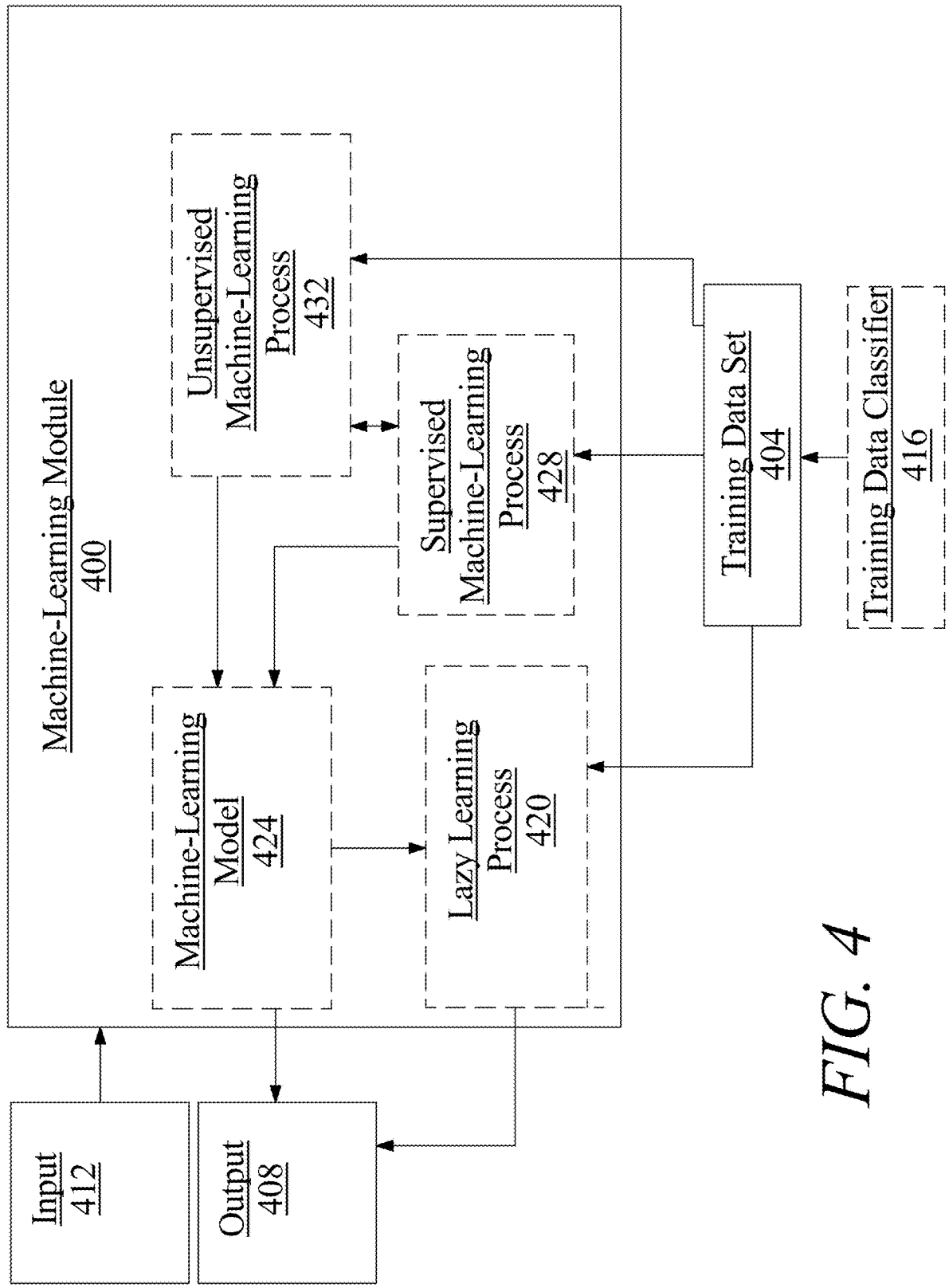
FIG. 4 is a block diagram illustrating an exemplary embodiment of a machine-learning module.

Referring now to FIG. 4, an exemplary embodiment of a machine-learning module 400 that may perform one or more machine-learning processes as described in this disclosure is illustrated. Machine-learning module may include any suitable machine-learning module which may perform determinations, classification, and/or analysis steps, methods, processes, or the like as described in this disclosure using machine learning processes. A "machine learning process," as used in this disclosure, is a process that automatedly uses training data set 404 containing training data 120 to generate an algorithm that will be performed by a computing device/module to produce outputs 408 given data provided as inputs 412; this is in contrast to a non-machine learning software program where the commands to be executed are determined in advance by a user and written in a programming language.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a process whereby a computing device and/or any module and/or component operating thereon derives a classifier from training data set 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to match one or more categories including elements of user data and/or constitutional data, such as without limitation a cohort of persons and/or other analyzed items and/or phenomena for which a subset of training data may be selected.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data set 404. Heuristic may include selecting some number of highest-ranking associations and/or training data set 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data set 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include identifications of meals 108 as described above as inputs, plurality of task chains 116 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data set 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 4, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data set 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data set 404.

Referring again to FIG. 1, computing device 104 may calculate a comprehensive quantifier 128 as a function of the plurality of constitutional component quantifiers 116. A "comprehensive quantifier," as described in this disclosure is a comprehensive metric, score, numerical value, function, or the like that summarizes a totality of user constitutional component quantifiers as it may relate to overall health, ability, and the like, of a user. For instance in non-limiting illustrative examples, a comprehensive quantifier 128 may refer to a user's overall general physical preparedness, which may be a combination of constitutional component metrics describing cardiovascular/respiratory endurance, stamina, strength, flexibility, power, speed, coordination, agility, balance, accuracy, explosiveness in movement, and anaerobic capacity, wherein each component may be measured, calculated, and/or otherwise described numerically by a component machine-learning model 124. In further non-limiting illustrative examples, a comprehensive quantifier 128 may be a single score, metric, function, vector, matrix, or the like, that numerically describes the user's general physical preparedness as a summation of all relevant constitutional components, such as the categories above. Calculating a comprehensive quantifier may include receiving comprehensive training data 120 including a plurality of entries correlating component quantifier data with comprehensive score data. Comprehensive training data 120 may include entries, metrics, numerical values, functions, and the like, retrieved by computing device 104 from expert submission, user database 112, for instance via a classifier containing a subset of cohort data, heuristic data, or the like; comprehensive training data 120 may be a series of entries retrieved from a research repository, peer-reviewed article, or the like that contains data relating how a plurality of user constitutional component quantifiers may be mathematically combined or otherwise relate to most accurately determining an overall score, rank, or quantification of user constitutional data. Computing device may train a comprehensive machine-learning model 132 as a function of the comprehensive training data 120 and calculate the comprehensive quantifier 128 as a function of the plurality of constitutional component quantifiers 116 and the comprehensive machine-learning model 132. A machine learning process would need to train with comprehensive training data 120, such as data from a medical professional, research paper, user database 112, online repository, or the like that may find relationships between the constitutional component quantifiers 116 and how they may be used to calculate a comprehensive quantifier that most accurately captures all component quantifier.

Figure 5:
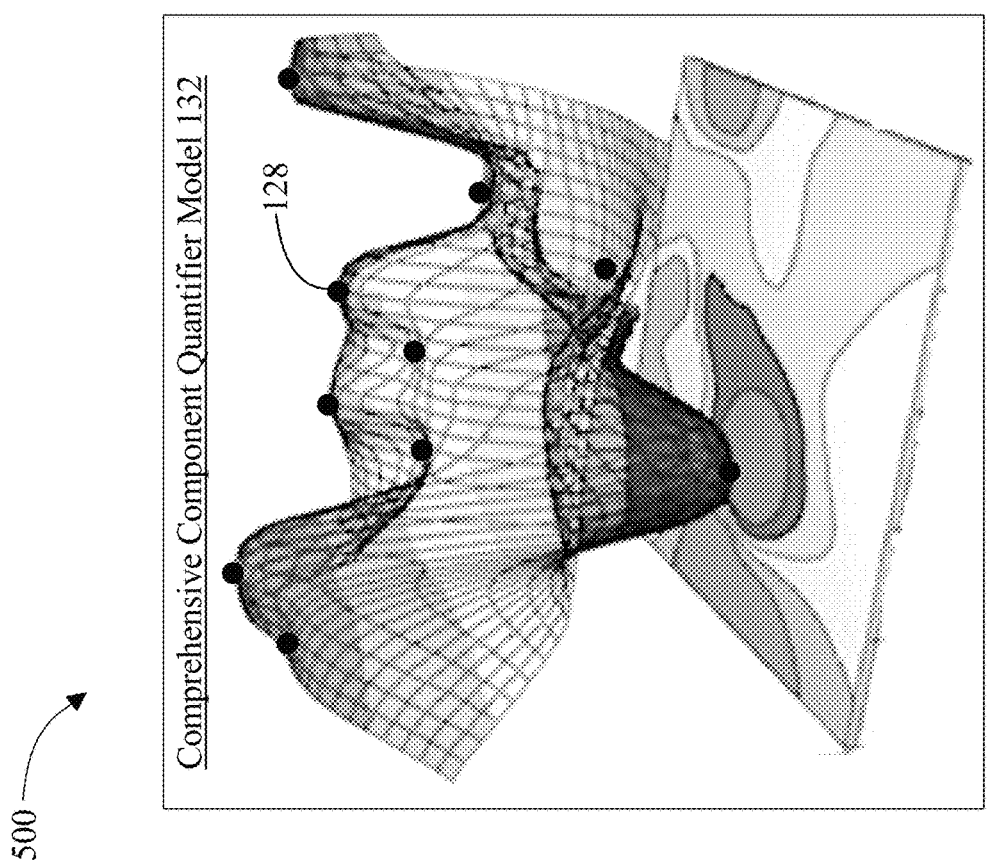
FIG. 5 is a diagrammatic representation of an exemplary embodiment of a comprehensive quantifier.

Referring now to FIG. 5, an exemplary embodiment 500 of a comprehensive component quantifier model 132, which may be trained as a function of a plurality of comprehensive training data 120, is illustrated. As illustrated in FIG. 5, each of the ten points (black spheres) represents constitutional quantifiers generated by a component machine-learning model 124. Each of the ten points may correspond to an individual comprehensive quantifier 128 generated by a component machine-learning model 124 and/or plurality of models. In the non-limiting illustrative example in FIG. 5, the comprehensive quantifiers 128 may refer to, for instance, cardiovascular/respiratory endurance, stamina, strength, flexibility, power, speed, coordination, agility, balance, explosiveness in movement, where each point is a numerical value corresponding to its contribution to the comprehensive metric of 'general physical preparedness'; the slopes between the points represent each of the relationships to each other variable, resulting in the 3-dimensional graphical landscape pictured. The machine-learning model generated may be depicted, wherein the peaks represent positive contributions to an overall score, and the troughs represent negative contributions to an overall score, and the areas under all peaks and troughs correspond to all relationships between each variable; this may be graphically represented as a system of functions in a 3-dimensional Gaussian distribution, such as the 3-dimensional graphical landscape illustrated. These points may be represented, for instance, as a matrix of values for a system of equations, or the like, that correspond to an overall value when, for instance the summation of the troughs are subtracted from the summation of the peaks, or the area under each curve is calculated as a deviation from a neutral score 'zero plane', as indicated by darker shades of grey. In such an example, the resulting comprehensive component quantifier may be a numerical value that corresponds to a user's general physical preparedness as it relates to a model trained with a combination of wearable device data, user-reported data, physiological data retrieved from a medical professional, and the like, as it corresponds to cardiovascular/respiratory endurance, stamina, strength, flexibility, power, speed, coordination, agility, balance, explosiveness in movement metrics.

Figure 6:
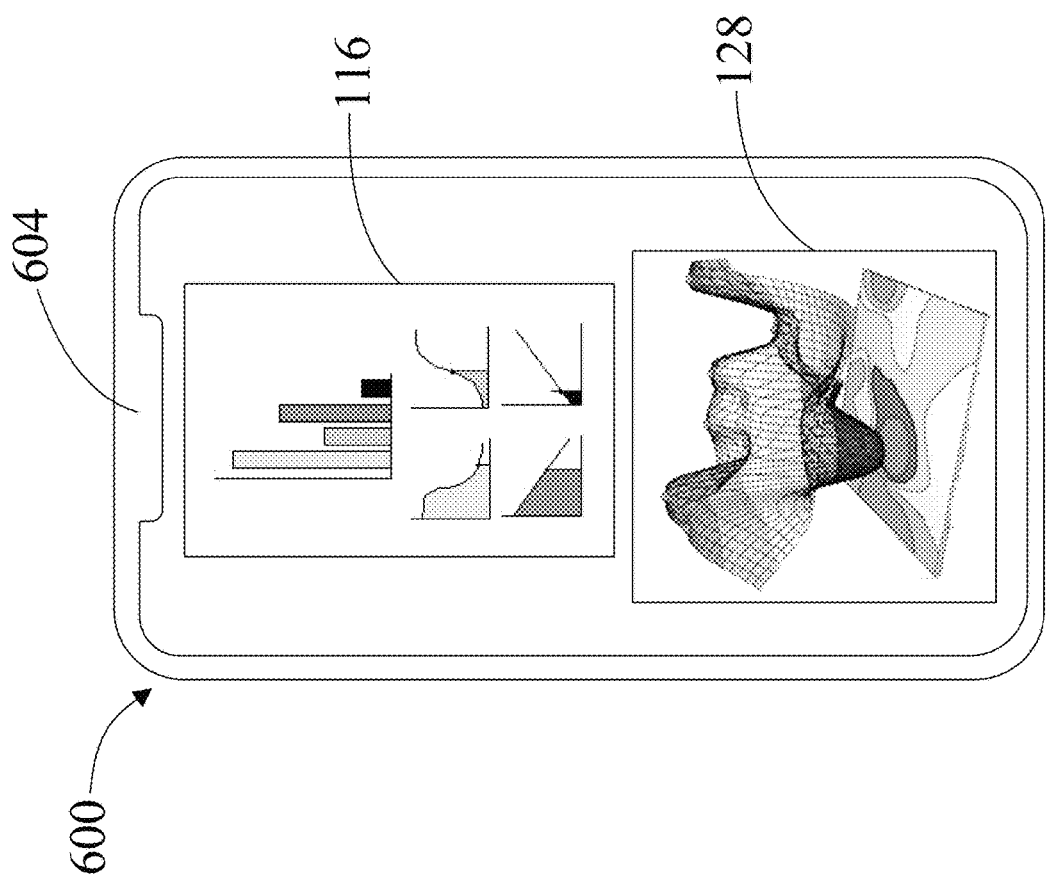
FIG. 6 is a diagrammatic representation an exemplary embodiment of a user device.

Referring now to FIG. 6, an exemplary embodiment 600 of a computing device 104 displaying, using a user device 604, the comprehensive quantifier 128 and the plurality of constitutional component quantifiers 116 is illustrated. User device 604 may communicate with computing device 104 via a user database 112, server, or the like, as described in further detail below. User device 604 may display comprehensive quantifiers 128, constitutional component quantifiers 116, and/or any associated data via a graphical user interface (GUI) and/or any other suitable means for displaying graphics, tables, text, or the like. User device 604 may prompt a user to input user constitutional data 108, or may prompt a user to transfer, upload, or otherwise communicate recorded wearable device data. Persons skilled in the art, upon reviewing the entirety of this disclosure, will be aware of various ways in which information may be displayed by a user device 604 and/or may prompt a user to enter data, and the various ways in which data may be entered via a user device 604.

Referring again to FIG. 1, computing device 104 may be configured to receive a user selection of at least a constitutional component quantifier 116. Computing device 104 may display and prompt user to select a constitutional component quantifier 116, as described above. Selecting a constitutional component qualifier 116 may be performed by a user to selectively target, improve, or otherwise change the metric, numerical value, score, rank or any other information associate with a qualifier. Selecting a constitutional component qualifier 116 may include, for instance and without limitation, checking-off a box or webpage demarcation, clicking a hyperlinked text, hover over, textual display, selecting a graphic, or the like. Persons skilled in the art, upon reviewing the entirety of this disclosure, will be aware of various ways in which data may be displayed by a computing device 104 and/or may prompt a user to select or otherwise specify selection of options, data, and the like.

Continuing in reference to FIG. 1, computing device 104 may collect user activity data, wherein collecting user activity data may include collecting user activity data via a client device 604 as a function of at least a constitutional component quantifier 116. User activity data may be the same type, kind, or style of data as user constitutional data 108, as described above. Computing device 104 may collect user activity data after a user has selected a constitutional component quantifier 116. Computing device 104 may collect user activity data, for instance and without limitation, via a wearable device wherein the wearable device has data stored and communicated via a variety of electronic data transfer methods including Bluetooth, wireless data transfer for instance via a web-based application, physical data transfer for instance via a USB device or external hard drive, and the like. Wearable device data may include numerical data, quantitative data, and/or qualitative data, that may be associated with signifiers, alphanumerical codes, or otherwise batched, tagged, or attached to date relating to user activity recorded by the device. Computing device 104 may collect user activity data that does not originate form a wearable device, such as user-reported data input via a client device 604, data supplied by a medical professional, researcher, lab technician, caregiver, or the like, either by retrieval from a user database 112, input via a web-based application, among other sources.

Continuing in reference to FIG. 1, computing device 104 may train an activity machine-learning model 136 as a function of the collected user activity data as training data 120 and identify a user program 140 that includes activities a user may adopt to improve constitutional component qualifiers 116. An activity machine-learning model 136 may be generated by a machine learning module 300 and trained using training data 120, as described above. Training data 120 may relate to collected user activity data that is provided, obtained, or otherwise collected by and/or retrieved from a user database 112 by a computing device 104 after a user was provided a first constitutional component quantifier 116. An activity machine-learning model 136 may be the same type of model as a comprehensive machine-learning model 132 and/or a component machine-learning model 124. An activity machine-learning model 136 may model, depict, or otherwise function is a similar manner as the aforementioned machine-learning models, for instance and without limitation, as described above and illustrated in FIG. 4-5. In non-limiting illustrative examples, an activity machine-learning model 136 may provide a program 140, wherein the program 140 details a series of activities that the model has determined a function, matrix, series of linear equations, or the like, that describes some level of the activity, including intensity, magnitude, and duration of the activity and the effect it is anticipated to have an the user constitutional component qualifier 116. An activity machine-learning model 136 may retrieve and/or store such activities from, for instance, a user database 112, online repository, research database, of the like. An activity machine-learning model 136 may be trained with user activity data to identify a user activity that a user may have already performed for continuing to improve a constitutional component qualifier. Alternatively or additionally, the activity machine-learning model 136 trained with user data may have identified a new user activity for a program 140 that outpaces a current user activity for purposes of improving a quantifier.

Continuing in reference to FIG. 1, computing device 104 may identify a user program 140. Computing device 104 may identify user program 140 activities using an activity machine-learning model 136 which may calculate and/or determine a ranking of a plurality of activities of a program 140 as a function of impact on a user score using a ranking function. Alternatively or additionally, computing device 104 may store and/or retrieve activity options from a user database 112 and prompt a user to select an option, or plurality of options, to form a program. As described herein, an activity machine learning model 136 may use a ranking function, wherein a ranking function may be a type of objective function that provides a rank, wherein the rank is based on a severity, impact, chronological steps in completing a task, difficulty, or the like. A "ranking function," as described herein may refer to an objective function, wherein an objective function may include performing a greedy algorithm process. A "greedy algorithm" is defined as an algorithm that selects locally optimal choices, which may or may not generate a globally optimal solution, and then such a ranking function would then rank the activities of the program 140 based upon the optimal listing. For instance, computing device 104 may select program activities so that scores associated therewith are the best score for ranking each activity, wherein the score relates to a numerical impact, and the ranking is based on increasing impact score.

Alternatively or additionally, in non-limiting illustrative examples a ranking function may be a linear objective function, wherein the computing device 104 may solve using a linear program, such as without limitation, a mixed-integer program. A "linear program," as used in this disclosure, is a program that optimizes a linear objective function, given at least a quantifier and/or ranking score based on impact of an activity on a quantifier; a linear program may be referred to without limitation as a "linear optimization" process and/or algorithm. For instance, in non-limiting illustrative examples, a linear program may use a linear objective function to calculate impact for a level of performing an activity on a constitutional component quantifier and rank the activities accordingly. A mathematical solver may be implemented to solve for the set of activities that maximizes impact scores; mathematical solver may be implemented on computing device 104 and/or another device in system 100, and/or may be implemented on third-party solver. A ranking function may include minimizing a loss function, where a "loss function" is an expression an output of which a ranking process minimizes to generate an optimal result. As a non-limiting example, computing device 104 may assign variables relating to a set of parameters, which may correspond to impact score components and quantifier score components, as described above, calculate an output of mathematical expression using the variables, and select an objective, or set of activities, that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs. Persons skilled in the art, upon reviewing the entirety of this disclosure, will be aware of various embodiments in which a ranking function may take form and be used by an activity machine-learning model 136 to rank activities of a program 140 based on some criteria as it relates to a user score.

Continuing in reference to FIG. 1, computing device 104 may regenerate at least a constitutional component quantifier 116 as a function of the user activity data, wherein regenerating the constitutional component quantifier 116 may include determining, using the component machine-learning model 124 and user activity data, an impact of the user activity data on at least a constitutional component quantifier 116, and calculating at least an updated constitutional component quantifier 144 as a function of the user activity data. Regenerating a constitutional component quantifier 144 may include recalculating an updated quantifier using the original quantifier as an input and a component machine-learning model 124 trained to model how the quantifier is affected by user activity data. Alternatively or additionally, an activity machine-learning model 136 may also determine an impact, degree, magnitude, or the like, that a user activity has on a quantifier, and the computing device 104 using a machine learning process, as described above, may update the component machine-learning model 124 using the outputs generate from an activity machine-learning model 136 to recalculate a quantifier.

Continuing in reference in FIG. 1, computing device 104 may recalculate the comprehensive quantifier 128 as a function of the recalculated constitutional component quantifier 144. Recalculating a comprehensive quantifier 128 may include using a first comprehensive machine-learning model 132; likewise a second comprehensive machine-learning model 132 may be generated by a machine-learning process with updated training data 120, wherein updated training data 120 reflects changes in patterns, heuristics, and the like attributed to user activity data and its relationship to recalculated constitutional component quantifiers 116 and the anticipated effects this may have on the comprehensive quantifier 128, as described above.

Continuing in reference to FIG. 1, recalculating the comprehensive quantifier 128 as a function of the recalculated constitutional component quantifier 144 may include using the comprehensive machine-learning model 132 to calculate an updated comprehensive quantifier 148 as a function of at least an updated constitutional component quantifier 144 and a first constitutional component quantifier 116. A comprehensive machine-learning model 132 may accept an input of a first constitutional component quantifier 116 and use a model trained, as described above, to recalculate any effects an updated comprehensive quantifier 148 may have on a comprehensive quantifier 128 as a function of at least an updated constitutional component quantifier 144. At least an updated constitutional component quantifier 144 may include more than one quantifier of a plurality of quantifiers, wherein at least one is updated to reflect any changes from user activity data. In non-limiting illustrative examples, an updated comprehensive quantifier 148 output by a comprehensive machine-learning model 132 may be the same as a first constitutional component quantifier 128. In further non-limiting illustrative examples, user activity data may detail, for instance, increased physical activity which has resulted in improved scores in updated constitutional component quantifiers 144 relating to body mass index, resting heart rate, and cardiovascular endurance, which a comprehensive machine-learning model 132 may take as an input, retrieve a first comprehensive quantifier 128 relating to the user from the user database 112 and output an updated comprehensive quantifier 148 with an improved overall score reflecting the improved scores.

Continuing in reference to FIG. 1, computing device 104 may display the updated constitutional component quantifier 148 to a user. For instance, computing device 104 may display the updated constitutional component quantifier 148 via a user device 604, as described above and in further detail below.

Continuing in reference to FIG. 1, displaying the updated constitutional component quantifier 148 to a user further comprises receiving user selection of a program 140 corresponding to a change in a constitutional component quantifier 116, and matching, using the component machine-learning model 132, user activity data to the program 140 for user score 152 recalculation. In non-limiting illustrative examples, displaying the updated constitutional component quantifier 148 to a user may be done, for instance by a user device 604, and may include prompting a user for selection of a program 140 corresponding to a change in a constitutional component quantifier 116, wherein a user may select a program 140 output by an activity machine-learning model 136. A component machine-learning model 132 trained with training data 120 that corresponds to user activity data, may accept an input of a user-selected program 140 and calculate how a user's activity corresponds to a selected program 140. A component machine-learning model 132 may determine if a user activity fulfilled an entire program 140, portion of a program 140, or was an activity that improved a quantifier, but fell outside the purview of a program 140. A component machine-learning model 132 may use this information for user score 152 recalculation, wherein recalculating user score 152 may reflect if a user completed any portion of a program 140 in changing their constitutional component quantifier 116. In further non-limiting illustrative examples, a user score 152 may increase in differing amounts if a user activity improved a constitutional component quantifier 116 to the updated constitutional component quantifier 144 using a program 140 rather than activities outside the purview of the program 140. In such an example, a user score 152 may benefit from a score increase, but with a trade-off corresponding to not sticking to a user-selected program 140.

Continuing in reference to FIG. 1, matching user activity data to the program 140 for recalculation may include tracking, using an activity machine-leaning model 136, user progress in the program 140 as a function of user activity data as it relates to an updated constitutional component quantifier, generating an updated user score 152 that tracks how a user is adhering to the user program 140, and updating the user program 140 as a function of user progress. An activity machine-learning model 136 trained with training data 120 that corresponds to user activity data, may accept an input of user activity data and an updated constitutional component quantifier 144 and retrieve a first user-selected program 140 from a user database 122, and calculate how a user's activity corresponds to a selected program 140. For instance, an activity machine-learning model 136 may determine if a user activity fulfilled an entire program 140, portion of a program 140, or reported an activity that fell outside the purview of a program 140. An activity machine-learning model 136 may use this information for user score 152 recalculation, wherein recalculating user score 152 may reflect if a user completed any portion of a program 140 in changing their constitutional component quantifier 116. In non-limiting illustrative examples, a user score 152 may benefit from a score increase despite any positive change in a constitutional component quantifier 116 because the user has not abandoned the program 140 according to the tracked user activity. The activity machine-learning model 136 may update the user program 140 as a function of user progress, for instance, by eliminating an activity as it has been completed, inserting a new step that follows a first activity, or the like. In non-limiting illustrative examples, a second activity that is added to a program 140 by an activity machine-learning model 136 may be the same as a first activity, chronologically related to a first activity, increased in difficulty than a first activity, or the like. An activity machine-learning model 136 may otherwise adjust a program 140 depending on how user activity tracks to a program 140, and how a program is improving a user score 152 as a function of user progress of said program 140.

Continuing in reference to FIG. 1, updating the user program may include generating an updated ranking of a plurality of activities of the updated user program 156 as a function of impact on a user score using a ranking function. An activity machine-learning model 136 may generate an updated user program 156 using a first program 140 and how user activity tracks to a program 140 and an associated user score 152. Generating an updated user program 156 may include ranking the activities relating to a program. Activities may be ranked according to difficulty, chronological ordering, likelihood of a user following the activity, ease of adoption of activity by a user, and/or a combination of these ranking factors and others, as described in further detail below.

Continuing in reference to FIG. 1, computing device 104 may update the user program 140 by using a scoring function to recalculate a user score 152 as a function of program progress, wherein a scoring function may include improving user score 152 for activities that correspond to adhering to a user program 140, and penalizing a user score 152 for failing to adhere to a user program 140. Using a scoring function may include optimizing an objective function as a function of the effect past user activities have on comprehensive quantifiers 128, as described above. A scoring function may relate the magnitude of effect a user activity may have on a user score 152 as a function of how well it adheres to a user program 140. In non-limiting illustrative examples, a user score 152 may be improved by a user activity that adhered well to a program and/or did not adhere, but improved a comprehensive quantifier 128; a user score 152 may decrease as a penalty for a user not adhering to a program 140, regardless of a positive change in comprehensive quantifier 128. A scoring function may be used in ranking a plurality of program 140 activities based upon how adhering to an activity may improve and/or penalize user score 152. Alternatively or additionally, a scoring function may be used to rank program 140 activities in generating an updated user program 156 in combining factors such as how adhering to an activity may improve and/or penalize user score 152 and the anticipated difficulty in a user adhering to a program, among other factors, to recalculate corrected, weighed, or otherwise modified scoring.

Figure 7:
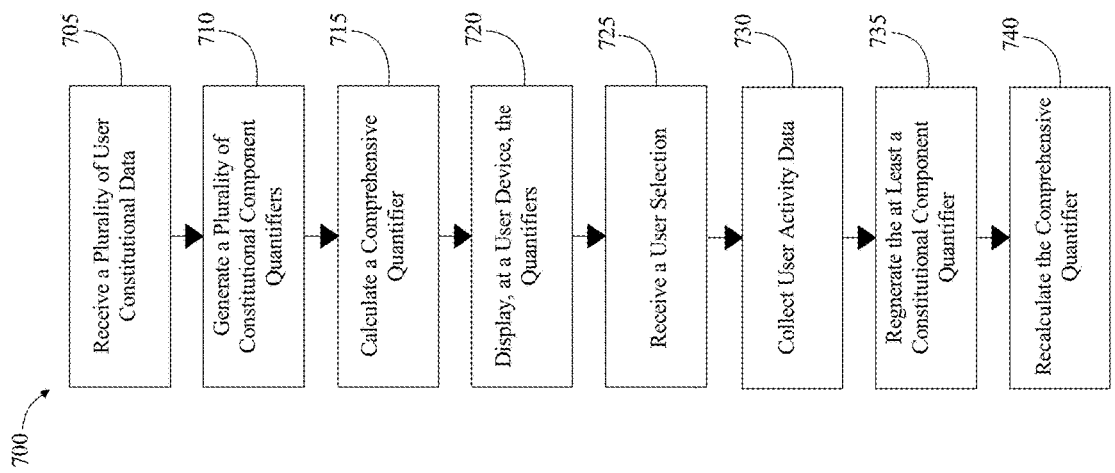
FIG. 7 is a flow diagram illustrating an exemplary workflow of a method of an interactive system for activity quantification.

Referring now to FIG. 7, an exemplary embodiment of a method 700 for activity quantification is illustrated. At step 705, a computing device 104 may be configured to receive a plurality of user constitutional data 108. User constitutional data 108 may include at least an element of user-reported data from a questionnaire, and/or at least an element of data retrieved from a wearable device, as described herein; this may be implemented, without limitation, as described above in reference to FIGS. 1-6.

At step 710, computing device 104 may generate a plurality of constitutional component quantifiers 116, wherein generating each constitutional component quantifier 116 may include receiving component training data 120, the component training data 120 including a plurality of entries correlating constitutional data with component quantifier data, training a component machine-learning model 124 as a function of the component training data 120, and generating the constitutional component quantifier 116 as a function of the user constitutional data and the component machine-learning model 124; this may be implemented, without limitation, as described above in reference to FIGS. 1-6.

At step 715, computing device 104 may calculate a comprehensive quantifier 128 as a function of the plurality of constitutional component quantifiers 116, wherein calculating may include receiving comprehensive training data 120, the comprehensive training data 120 including a plurality of entries correlating component quantifier data with comprehensive score data, training a comprehensive machine-learning model 132 as a function of the comprehensive training data 120, and calculating the comprehensive quantifier 128 as a function of the plurality of constitutional component quantifiers and the comprehensive machine-learning model 132; this may be implemented, without limitation, as described above in reference to FIGS. 1-6.

At step 720, computing device 104 may display, at a user device 604, the comprehensive quantifier 128 and the plurality of constitutional component quantifiers 116; this may be implemented, without limitation, as described above in reference to FIGS. 1-6.

At step 725, computing device 104 may receive a user selection of at least a constitutional component quantifier 116; this may be implemented, without limitation, as described above in reference to FIGS. 1-6.

At step 730, computing device 104 may collecting user activity data. Collecting user activity data may include collecting user activity data via a client device as a function of at least a constitutional component quantifier 116, training an activity machine-learning model 136 as a function of the collected user activity data, and identifying a user program 140 that includes activities a user may adopt to improve constitutional component qualifiers 116. Identifying a user program 140 using an activity machine-learning model 136 may include ranking a plurality of activities of a program as a function of impact on a user score using a ranking function; this may be implemented, without limitation, as described above in reference to FIGS. 1-6.

At step 735, computing device 104 may regenerate the at least a constitutional component quantifier 116 as a function of the user activity data. Regenerating the at least a constitutional component quantifier 116 as a function of the user activity data may include determining, using a component machine-learning model 124 and user activity data, an impact of the user activity data on at least a constitutional component quantifier 116, and calculating at least an updated constitutional component quantifier 144 as a function of the user activity data; this may be implemented, without limitation, as described above in reference to FIGS. 1-6.

At step 740, computing device 104 may recalculate the comprehensive quantifier as a function of the recalculated at least a constitutional component quantifier. Recalculating the comprehensive quantifier as a function of the recalculated at least a constitutional component quantifier may include using a comprehensive machine-learning model 132 to calculate an updated comprehensive quantifier 148 as a function of at least an updated constitutional component quantifier 144 and a first constitutional component quantifier 116, and displaying the updated constitutional component quantifier 144 to a user. Displaying the updated constitutional component quantifier 144 to a user may include receiving user selection of a program 140 corresponding to a change in a constitutional component quantifier 116, and matching, using the component machine-learning model, user activity data to the program 140 for user score recalculation. Matching user activity data to the program 140 for recalculation may include tracking, using an activity machine-leaning model 136, user progress in the program 140 as a function of user activity data as it relates to a recalculated constitutional quantifier, generating an updated user score 152 that tracks how a user is adhering to the user program 140, and updating the user program 140 as a function of user progress. Updating the user program 140 may include generating an updated ranking of a plurality of activities of the updated user program 140 as a function of impact on a user score 152 using a ranking function. Updating the user program may include using a scoring function to recalculate a user score as a function of program progress, wherein a scoring function may include optimizing an objective function as a function of the effect past user activities have on comprehensive quantifiers, improving user score 152 for activities that correspond to adhering to a user program, and penalizing a user score for failing to adhere to a user program; this may be implemented, without limitation, as described above in reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
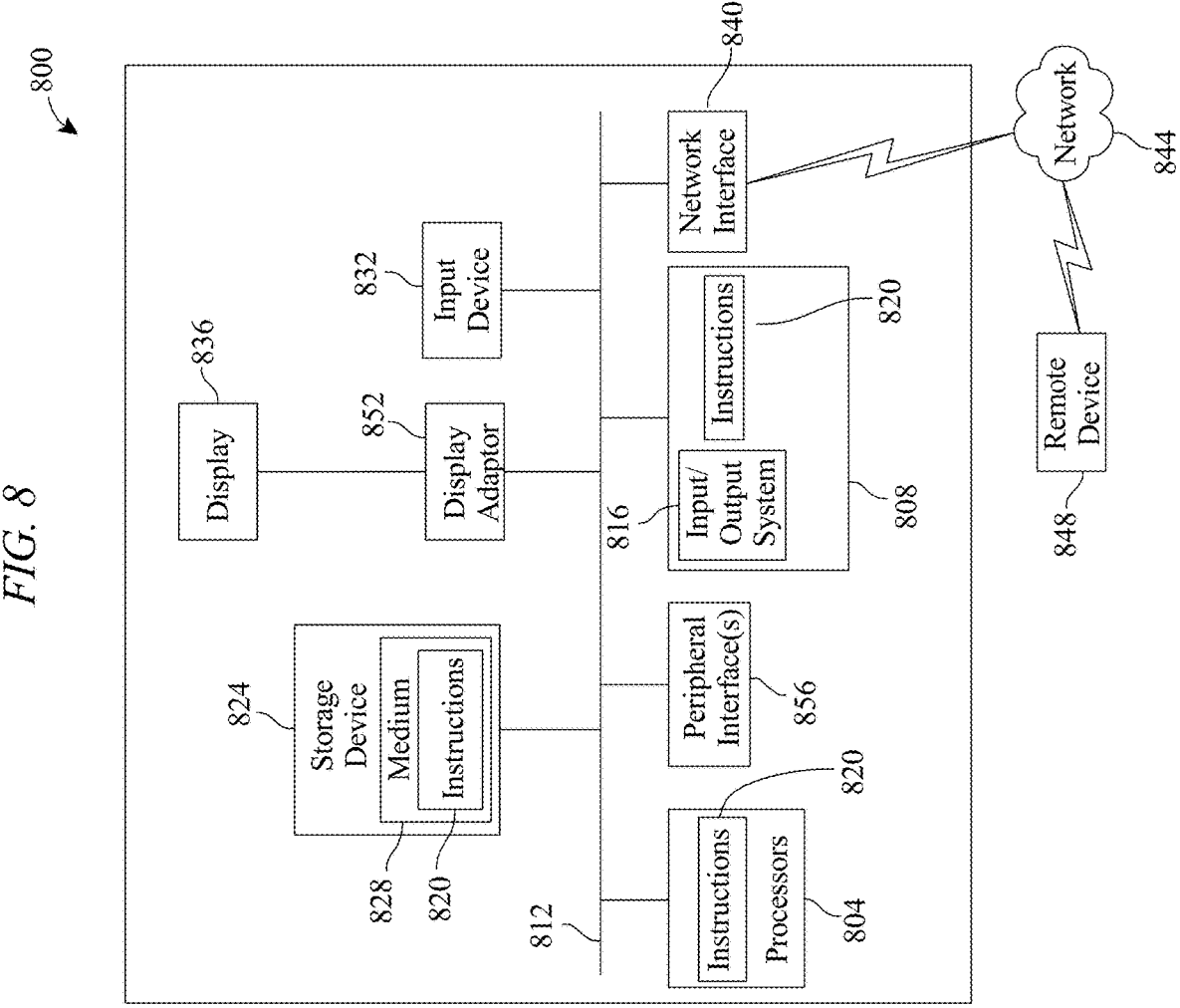
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An interactive system for activity quantification, the system comprising a computing device, wherein the computing device is configured to:
   receive a plurality of user constitutional data;
   generate a plurality of constitutional component quantifiers, wherein generating each constitutional component quantifier further comprises:
      receiving component training data, the component training data including a plurality of entries correlating constitutional data with constitutional component quantifier data;
      training a component machine-learning model as a function of the component training data; and
      generating the trained constitutional component quantifier as a function of the user constitutional data and the component machine-learning model;
   calculate a comprehensive quantifier as a function of the plurality of constitutional component quantifiers, wherein the comprehensive quantifier comprises a comprehensive quantifier model comprising at least one peak representing at least one first constitutional component quantifiers with positive contributions to the comprehensive quantifier and at least one trough representing second constitutional component quantifiers with negative contribution to the comprehensive quantifier and calculating further comprises:
      receiving comprehensive training data, the comprehensive training data including a plurality of entries correlating constitutional component quantifier data with comprehensive quantifier data;
      training a comprehensive machine-learning model as a function of the comprehensive training data;
      calculating the comprehensive quantifier as a function of the plurality of constitutional component quantifiers and the trained comprehensive machine-learning model;
      updating the comprehensive training data as a function of the plurality of constitutional component quantifiers and the comprehensive quantifier; and
      retraining the comprehensive machine-learning model as a function of the updated comprehensive training data;
   display, at a user device, the comprehensive quantifier and the plurality of constitutional component quantifiers;
   receiving a user selection of at least a constitutional component quantifier;
   collect user activity data;
   regenerate the at least a constitutional component quantifier as a function of the user activity data; and
   recalculate the comprehensive quantifier as a function of the regenerated at least a constitutional component quantifier.

2. The system of claim 1, wherein user constitutional data further comprises:
   at least an element of user-reported data from a questionnaire; and
   at least an element of data retrieved from a wearable device.

3. The system of claim 1, wherein collecting user activity data further comprises:
   collecting user activity data via a client device as a function of at least a constitutional component quantifier;
   training an activity machine-learning model as a function of the collected user activity data; and
   identifying a user program that includes a plurality of activities a user may adopt to improve constitutional component qualifiers, as a function of the activity machine-learning model and the user activity data.

4. The system of claim 3 further comprising ranking the plurality of activities as a function of impact on a user score using a ranking function.

5. The system of claim 1, wherein regenerating the at least a constitutional component quantifier as a function of the user activity data further comprises:
   determining, using the component machine-learning model and user activity data, an impact of the user activity data on at least a constitutional component quantifier; and
   calculating at least an updated constitutional component quantifier as a function of the user activity data.

6. The system of claim 5, wherein recalculating the comprehensive quantifier further comprises:
   calculating, using the comprehensive machine-learning model, an updated comprehensive quantifier as a function of at least an updated constitutional component quantifier.

7. The system of claim 1, wherein receiving the user activity data further comprises:
   receiving user selection of a program for changing a constitutional component quantifier; and
   matching user activity data to the program for user score recalculation.

8. The system of claim 7, wherein matching user activity data to the program for recalculation further comprises:
   tracking user progress in the program as a function of user activity data;
   generating an updated user score that tracks how a user is adhering to the user program; and
   updating the user program as a function of user progress.

9. The system of claim 8, wherein updating the user program further comprises generating an updated ranking of a plurality of activities of the updated user program as a function of impact on a user score using a ranking function.

10. The system of claim 9, wherein updating the user program further comprises:
    using a scoring function to recalculate a user score as a function of program progress, wherein a scoring function further comprises:
       incrementing the user score for activities that correspond to adhering to a user program; and
       decrementing the user score for failing to adhere to a user program.

11. A method for activity quantification, the system comprising a computing device, wherein the computing device is configured to:

receive a plurality of user constitutional data;
generate a plurality of constitutional component quantifiers, wherein generating each constitutional component quantifier further comprises:
  receiving component training data, the component training data including a plurality of entries correlating constitutional data with constitutional component quantifier data;
  training a component machine-learning model as a function of the component training data; and
  generating the constitutional component quantifier as a function of the user constitutional data and the component machine-learning model;
calculate a comprehensive quantifier as a function of the plurality of constitutional component quantifiers, wherein calculating further comprises:
  receiving comprehensive training data, the comprehensive training data including a plurality of entries correlating component quantifier data with comprehensive score data;
  training a comprehensive machine-learning model as a function of the comprehensive training data; and
  calculating the comprehensive quantifier as a function of the plurality of constitutional component quantifiers and the comprehensive machine-learning model;
displaying, at a user device, the comprehensive quantifier and the plurality of constitutional component quantifiers;
receiving a user selection of at least a constitutional component quantifier;
collecting user activity data;
regenerate the at least a constitutional component quantifier as a function of the user activity data; and
recalculate the comprehensive quantifier as a function of the recalculated at least a constitutional component quantifier.

12. The method of claim 11, wherein user constitutional data further comprises:
  at least an element of user-reported data from a questionnaire; and
  at least an element of data retrieved from a wearable device.

13. The method of claim 11, wherein collecting user activity data further comprises:
  collecting user activity data via a client device as a function of at least a constitutional component quantifier;
  training an activity machine-learning model as a function of the collected user activity data; and
  identifying a user program that includes activities a user may adopt to improve constitutional component qualifiers.

14. The method of claim 13, wherein identifying a user program using an activity machine-learning model further comprises ranking a plurality of activities of a program as a function of impact on a user score using a ranking function.

15. The method of claim 11, wherein regenerating the at least a constitutional component quantifier as a function of the user activity data further comprises:
  determining, using a component machine-learning model and user activity data, an impact of the user activity data on at least a constitutional component quantifier; and
  calculating at least an updated constitutional component quantifier as a function of the user activity data.

16. The method of claim 15, wherein recalculating the comprehensive quantifier as a function of the recalculated at least a constitutional component quantifier further comprises:
  using a comprehensive machine-learning model to calculate an updated comprehensive quantifier as a function of at least an updated constitutional component quantifier and a first constitutional component quantifier; and
  displaying the updated constitutional component quantifier to a user.

17. The method of claim 11, wherein displaying the updated constitutional component quantifier to a user further comprises:
  receiving user selection of a program corresponding to a change in a constitutional component quantifier; and
  matching, using the component machine-learning model, user activity data to the program for user score recalculation.

18. The method of claim 17, wherein matching user activity data to the program for recalculation further comprises:
  tracking, using an activity machine-leaning model, user progress in the program as a function of user activity data as it relates to a recalculated constitutional quantifier;
  generating an updated user score that tracks how a user is adhering to the user program; and
  updating the user program as a function of user progress.

19. The method of claim 18, wherein updating the user program further comprises generating an updated ranking of a plurality of activities of the updated user program as a function of impact on a user score using a ranking function.

20. The method of claim 19, wherein updating the user program further comprises:
  using a scoring function to recalculate a user score as a function of program progress, wherein a scoring function further comprises:
    improving user score for activities that correspond to adhering to a user program; and
    penalizing a user score for failing to adhere to a user program.

* * * * *